(12) United States Patent
Jumalon et al.

(10) Patent No.: US 12,257,332 B2
(45) Date of Patent: Mar. 25, 2025

(54) PREVENTION OF THE OXIDATION OF PERFUMERY RAW MATERIALS

(71) Applicant: Firmenich SA, Satigny (CH)

(72) Inventors: Janille Marie Jumalon, Plainsboro, NJ (US); Addi Fadel, Plainsboro, NJ (US); Michael Calandra, Plainsboro, NJ (US); Ying Wang, Plainsboro, NJ (US); Melanie Smith, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/768,103

(22) PCT Filed: Jan. 24, 2019

(86) PCT No.: PCT/EP2019/051758
§ 371 (c)(1),
(2) Date: May 29, 2020

(87) PCT Pub. No.: WO2019/145425
PCT Pub. Date: Aug. 1, 2019

(65) Prior Publication Data
US 2020/0289388 A1    Sep. 17, 2020

Related U.S. Application Data

(60) Provisional application No. 62/623,077, filed on Jan. 29, 2018.

(30) Foreign Application Priority Data

Apr. 27, 2018    (EP) .................................... 18169940

(51) Int. Cl.
*A61K 8/365*    (2006.01)
*A61Q 13/00*    (2006.01)

(52) U.S. Cl.
CPC .............. *A61K 8/365* (2013.01); *A61Q 13/00* (2013.01); *A61K 2800/10* (2013.01); *A61K 2800/522* (2013.01); *A61K 2800/524* (2013.01)

(58) Field of Classification Search
CPC .......... A61K 2800/10; A61K 2800/522; A61K 2800/524; A61K 8/36
See application file for complete search history.

(56) References Cited

U.S. PATENT DOCUMENTS

| | | | |
|---|---|---|---|
| 5,443,817 A * | 8/1995 | Zimmerman | A61Q 1/14 424/47 |
| 5,605,679 A * | 2/1997 | Hansenne | A61K 8/35 424/59 |
| 5,609,875 A | 3/1997 | Hadas | |
| 2002/0054923 A1* | 5/2002 | Suzuki | A61K 31/192 424/769 |
| 2003/0078186 A1 | 4/2003 | Denver | |
| 2006/0137109 A1* | 6/2006 | Umeno | A61Q 5/065 8/405 |
| 2007/0059250 A1* | 3/2007 | Ahmad | A61K 9/0034 424/45 |
| 2007/0079446 A1 | 4/2007 | Lupia et al. | |
| 2013/0045913 A1* | 2/2013 | Germaneau | A61K 8/37 252/589 |
| 2019/0046422 A1 | 2/2019 | Calandra et al. | |
| 2019/0142735 A1 | 5/2019 | Kim et al. | |

FOREIGN PATENT DOCUMENTS

| | | | | |
|---|---|---|---|---|
| DE | 2436468 A1 | 2/1976 | | |
| EP | 2236127 A1 | 10/2010 | | |
| JP | 2007515396 A | 6/2007 | | |
| WO | WO-2006005846 A1 * | 1/2006 | ............... | A61K 8/35 |
| WO | 2018/004212 A1 | 1/2018 | | |

OTHER PUBLICATIONS

Pubchem, 2-Oxoglutaric acid, accessed Dec. 13, 2021, pp. 1-78 (Year: 2021).*
Pefrume.com, (Jul. 5, 2015), pp. 1-6 (Year: 2015).*
Database GNPD Mintel Eau de Toilette MP2 Cosmetic Solutions dated Jan. 13, 2015; 7 pages.
Database GNPD Mintel Organic Cologne LIM Cosmetics dated Dec. 7, 2017; 2 pages.
Database GNPD Mintel Hydrating Sunscreen Lotion Da Bao Cosmetics dated Sep. 15, 2016; 3 pages.
Database GNPD Mintel Hydrating Sunscreen Lotion Da Bao Cosmetics dated Jul. 20, 2017: 4 pages.
Zhang Jian et al Journal of Zhejiang University Science B 2007 vol. 8 No. 2 p. 98-104 dated Feb. 1, 2007; 7 pages.
International Search Report and Written Opinion for International Application No. PCT/EP2019/051758 dated Mar. 4, 2019; 14 pages.

* cited by examiner

*Primary Examiner* — Andrew S Rosenthal
*Assistant Examiner* — Lyndsey M Beckhardt

(57) ABSTRACT

The aspects presented herein provide methods and compositions for the reduction of the peroxide value of perfume ingredients, formulated perfumes, formulated body care products, essential oils, and natural extracts.

6 Claims, 12 Drawing Sheets

Figure 11.

| Samples with vanillin levels from 0.25%- 2.00% | Average Initial pH and the range | Average pH after testing and the range | |
|---|---|---|---|
| Control with Red 33 | 6.60 (6.10 to 6.92) | 4.92 (4.83 to 4.97) | Δ pH = 1.68 |
| Red 33 +0.3% Covabsorb | 6.48 (6.15 to 6.82) | 5.08 (4.90 to 5.34) | Δ pH = 1.40 Slight improvement |
| Red 33 +0.30% Covabsorb +0.25% dilution of α-ketoglutaric acid formed by reacting α-ketoglutaric acid with NMDA | 6.42 (6.38 to 6.46) | 6.44 (6.33 to 6.52) | Δ pH = 0.02 Improvement |
| Red 33 +0.30% Covabsorb +0.10% Tinogard Q | 6.17 (6.10 to 6.27) | 5.51 (5.36 to 5.84) | Δ pH = 0.66 Slight improvement |
| Red 33 +0.30% Covabsorb +0.10% Tinogard Q +0.25% dilution of α-ketoglutaric acid formed by reacting α-ketoglutaric acid with NMDA | 6.43 (6.38 to 6.47) | 6.50 (6.43 to 6.56) | Δ pH = 0.07 Improvement |

PREVENTION OF THE OXIDATION OF PERFUMERY RAW MATERIALS

CROSS REFERENCE TO RELATED APPLICATIONS

This application is the national phase of PCT/EP2019/051758, filed on Jan. 24, 2019, and claims priority to U.S. provisional patent application 62/623,077, filed on Jan. 29, 2018, and EP application no. 18169940.6, filed on Apr. 27, 2018, the contents of which are hereby incorporated by reference in their entirety.

FIELD OF THE INVENTION

The various aspects presented herein relate to methods and compositions for the reduction, prevention, and/or inhibition of the oxidation of perfume ingredients, formulated perfumes, formulated body care products, cosmetic products, essential oils, and natural extracts.

BACKGROUND

Many perfume ingredients, formulated perfumes, body care products, cosmetic products, perfumery raw materials (such as, for example, essential oils, natural extracts, and synthetic ingredients) can undergo oxidation when exposed to the atmosphere, heat and/or light. The oxidation may lead to changes in the organoleptic properties, and/or the appearance of the perfume ingredient, formulated perfume, formulated body care product, essential oil, or natural extract. For example, oxidation may result in the formation of chemical species including peroxides, organic hydroperoxides, peroxyhemiacetals, hemiacetals, acetals, or transesterification products. The chemical species formed as a result of oxidation may alter the organoleptic properties or appearance of the perfume ingredient, formulated perfume, formulated body care product, essential oil, or natural extract, or, alternatively, be harmful, irritant, or allergenic.

LED lights in particular have been demonstrated to oxidize perfume ingredients, formulated perfumes, formulated body care products, essential oils, and natural extracts far more than other light sources. Consequently, there is a need to reduce the oxidation of perfume ingredients, formulated perfumes, formulated body care products, cosmetic products, essential oils, and natural extracts.

SUMMARY

One aspect presented herein provides a method,
wherein the method reduces, prevents, and/or inhibits the oxidation of a formulated perfume, body care product, cosmetic product, or perfumery raw material,
wherein the method comprises adding at least one α-oxocarboxylic acid to the formulated perfume, body care product, or perfumery raw material in an amount sufficient to reduce, prevent, and/or inhibit of the oxidation of the formulated perfume, body care product, cosmetic product, or perfumery raw material.

In one aspect, the method further comprises adding at least one stabilizer to the formulated perfume, body care product, cosmetic product, or perfumery raw material.

In one aspect, the method further comprises adjusting the pH of the formulated perfume, body care product, cosmetic product, or perfumery raw material to pH 5 to pH 7.5.

In one aspect, the amount sufficient of the at least one α-oxocarboxylic acid is sufficient to reduce, prevent, and/or inhibit a change in the pH of the formulated perfume, body care product, cosmetic product, or perfumery raw material.

In one aspect, the reduction, prevention, and/or inhibition of the oxidation reduces, prevents, and/or inhibits a discoloration of the formulated perfume, body care product, cosmetic product, or perfumery raw material.

In one aspect, the reduction, prevention, and/or inhibition of the change in the pH reduces, prevents, and/or inhibits a discoloration of the formulated perfume, body care product, cosmetic product, or perfumery raw material.

In one aspect, the reduction, prevention, and/or inhibition of the oxidation increases, enhances, and/or improves the stability and/or shelf life of the formulated perfume, body care product, cosmetic product, or perfumery raw material.

In one aspect, the reduction, prevention, and/or inhibition of the change in the pH increases, enhances, and/or improves the stability and/or shelf life of the formulated perfume, body care product, cosmetic product, or perfumery raw material.

One aspect presented herein provides a composition comprising a formulated perfume, body care product, cosmetic product, or perfumery raw material and at least one α-oxocarboxylic acid, wherein the α-oxocarboxylic acid is in present in the composition in an amount sufficient to reduce, prevent, and/or inhibit the oxidation of the formulated perfume, body care product, cosmetic product, or perfumery raw material.

In one aspect, the composition further comprises at least one stabilizer.

In one aspect, the concentration of the at least one stabilizer in the composition is from 0.01 to 2 wt %.

In one aspect, the at least one stabilizer is selected from the group consisting of: butyl methoxydibenzoyl methane, ethylhexyl methoxycinnamate, ethylhexyl salicylate, tris(tetramethylhydroxypiperidinol) citrate, and mixtures thereof.

In one aspect, the at least one α-oxocarboxylic acid is selected from the group consisting of: pyruvic acid, 2-oxovaleric acid, phenylglyoxylic acid, 2-oxobutyric acid, 2-oxo-2-furanacetic acid, α-ketoglutaric acid, 2-oxopentandioate, oxaloacetic acid, indole-3-pryruvic acid, and mixtures thereof.

In one aspect, the amount sufficient of the at least one α-oxocarboxylic acid is from 0.0001 to 10 weight percent of the formulated perfume, body care product, cosmetic product, or perfumery raw material.

In one aspect, the at least one α-oxocarboxylic acid is added to the formulated perfume, body care product, cosmetic, or perfumery raw material as an organic salt.

In one aspect, the at least one α-oxocarboxylic acid is added to the formulated perfume, body care product, cosmetic, or perfumery raw material as a salt of a mono or divalent cation.

BRIEF DESCRIPTION OF THE FIGURES

FIG. 11 shows the effect of compositions according to certain aspects presented herein on the light-induced changes in the pH of a perfuming composition.

DETAILED DESCRIPTION

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Many formulated perfumes, body care products, cosmetic products, perfumery raw materials (such as, for example, essential oils, natural extracts, and synthetic ingredients) can undergo oxidation, resulting in oxidative damage or degradation. Referring to FIGS. 1 to 4, hydroalcohol solutions, such as formulated perfumes are oxidized following prolonged exposure to light or heat. Frequently, the locations where formulated perfumes are displayed contain lights, such as LED lights that are especially prone to oxidize formulated perfumes (see, for example, FIG. 1).

Without intending to be limited to any particular theory, the prolonged light exposure results in the formation of chemical species including peroxides, organic hydroperoxides, peroxyhemiacetals, or transesterification products. These intermediates may chemically modify the perfume ingredient(s) themselves, the dyes used to impart a color to the formulated perfume, or any combination thereof. Thus, the oxidation may lead to changes in the organoleptic properties, pH and/or the appearance of the perfume ingredient, formulated perfume, formulated body care product, essential oil, or natural extract.

Figure 1:
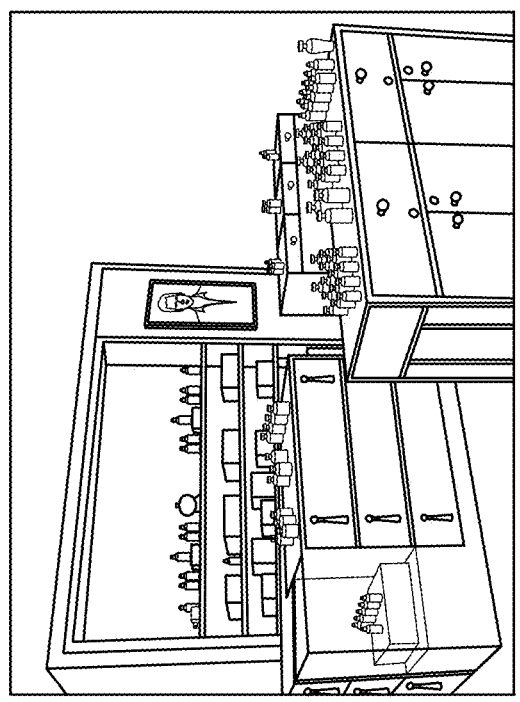
FIG. 1 shows a typical display for formulated perfumes, body care products, cosmetic products, or perfumery raw materials according to certain aspects presented herein.
Figure 1:
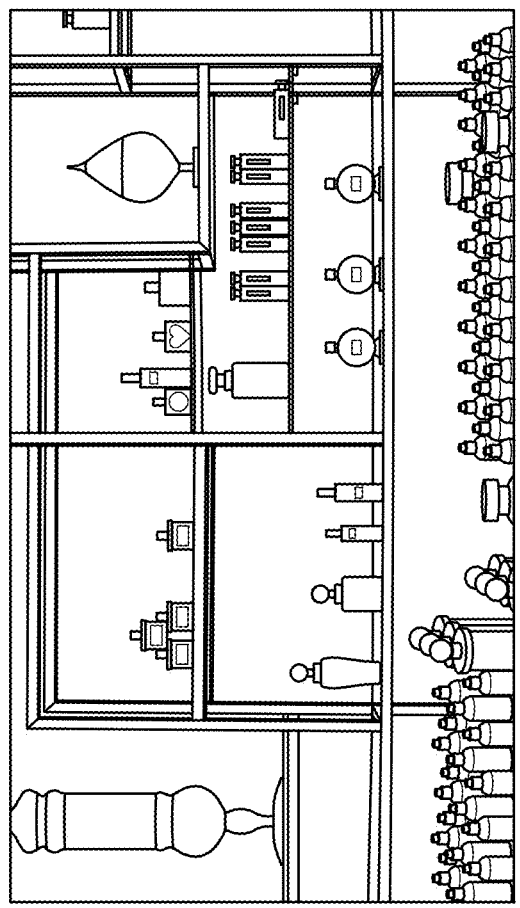
Figure 2:
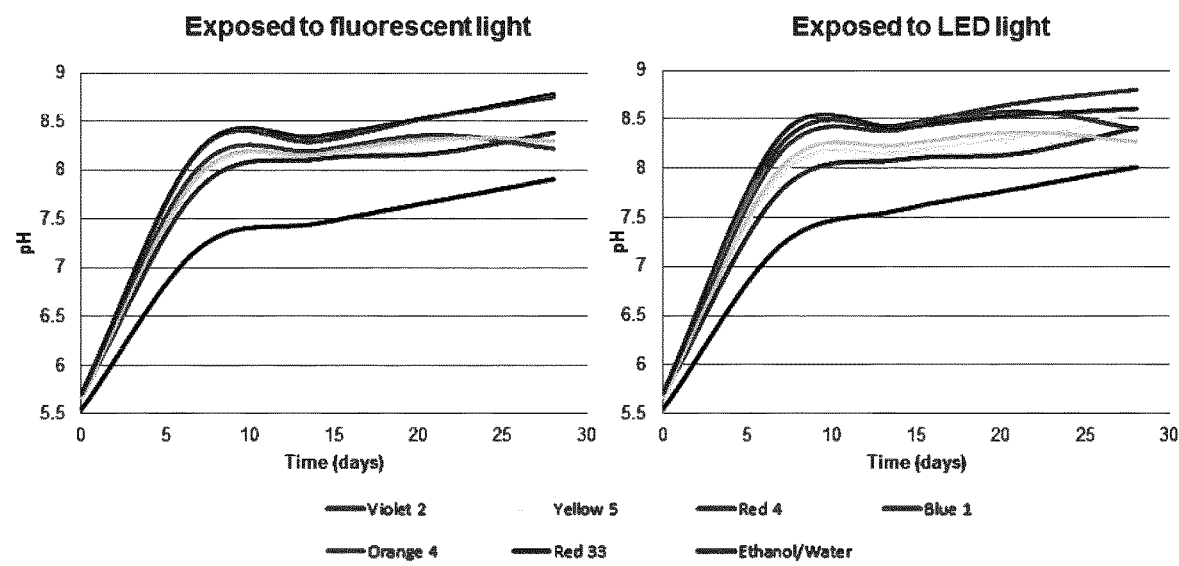
FIG. 2 shows the effect of the light source on the light-induced changes in formulated perfumes, body care products, cosmetic products, or perfumery raw materials over time.
Figure 3:
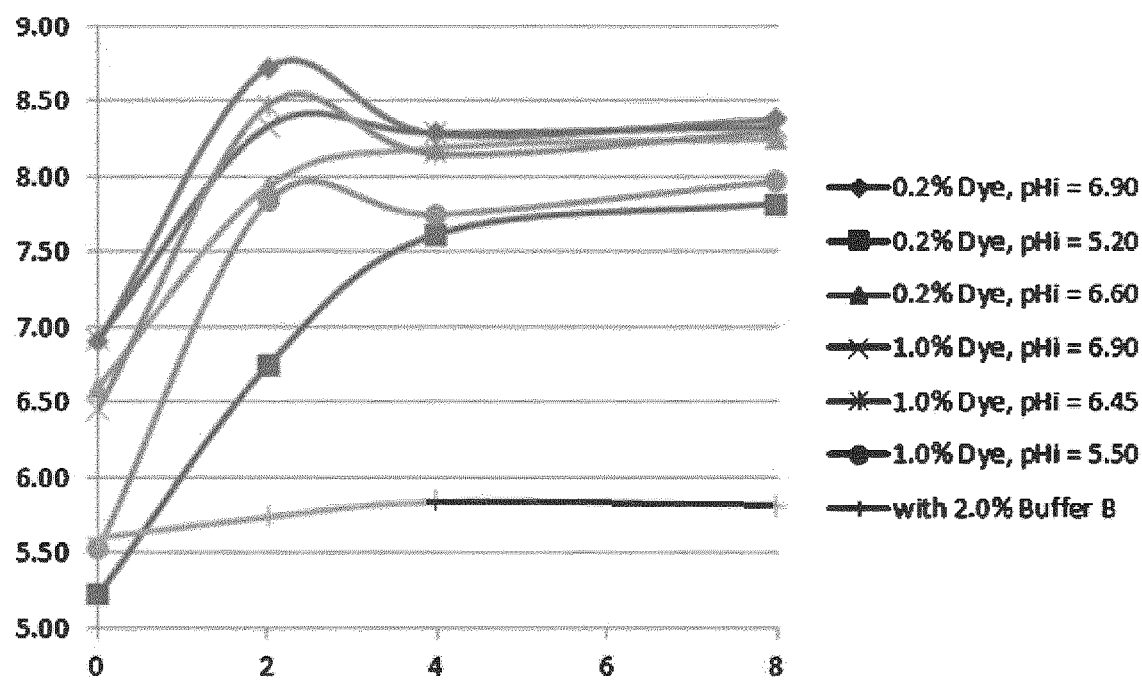
FIG. 3 shows the effect of a buffer on the light-induced change in pH of formulated perfume over time.
Figure 4:
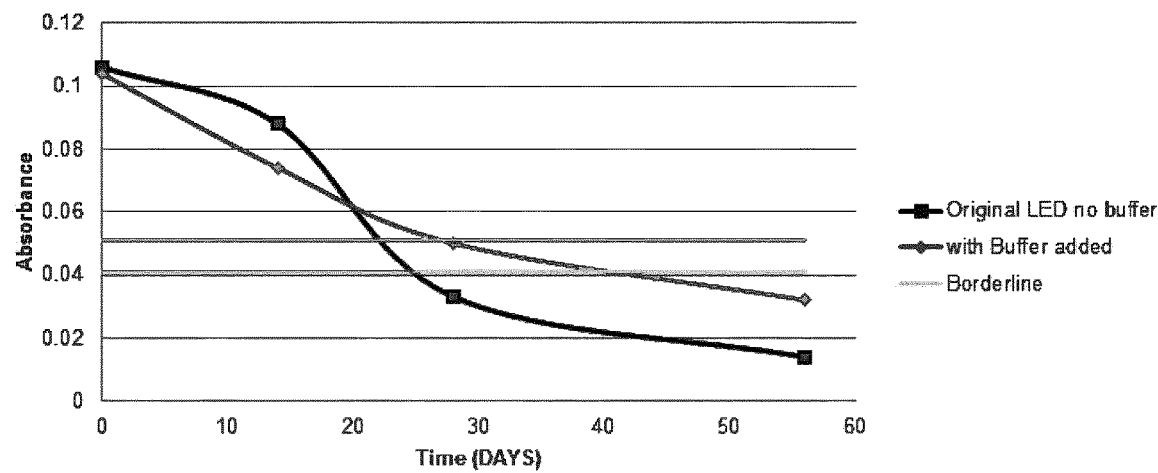
FIG. 4 shows the effect light-induced change in absorbance recorded at a wavelength of 530 nm of formulated perfume over time.

By way of illustration, prolonged light exposure may result in changes in the pH of a hydroalcoholic solution comprising a dye, simulating a formulated perfume (FIG. 2). The magnitude of the change in pH may depend on several factors, such as, for example, the type and concentration of the dyes included in the formulated perfume (FIGS. 2 and 3), the intensity and/or the type of light source (FIG. 2), the presence of buffers (FIG. 4), the composition of the formulated perfume, and the like.

In another illustrative example, oxidation may result in the formation of chemical species including peroxides, organic hydroperoxides, peroxyhemiacetals. The peroxide value (POV), defined as the amount of equivalents of oxidizing potential per 1 kilogram of material may be used as an indication of the extent of the oxidation.

The POV of formulated perfumes, body care products, cosmetic products, or perfumery raw materials is subject to regulatory limits, due to skin sensitization issues, such as, for example, contact dermatitis.

Consequently, there is a need to reduce, prevent, or remediate the oxidation of perfume ingredients, formulated perfumes, formulated body care products, cosmetic products, essential oils, and natural extracts.

Without intending to be limited to any particular theory, the oxidation of a formulated perfume, body care product, cosmetic product, or perfumery raw material is reduced, prevented, remediated, and/or inhibited by treating the formulated perfume, body care product, cosmetic product, or perfumery raw material with at least one α-oxocarboxylic acid.

Figure 5:
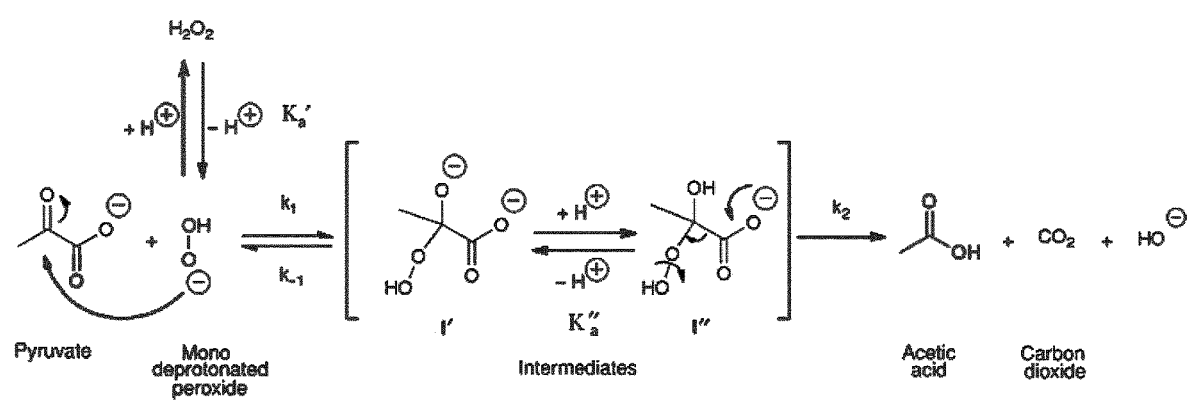
FIG. 5 shows an exemplar proposed oxidative decarboxylation reaction according to certain aspects presented herein.
Figure 6:
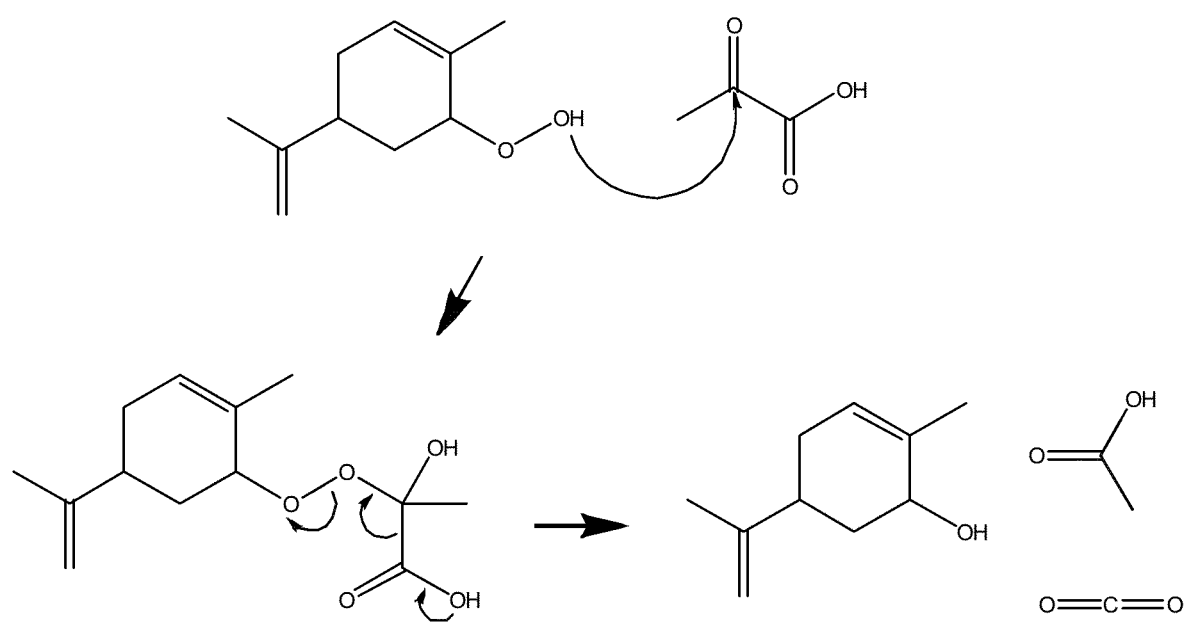
FIG. 6 shows an exemplar proposed reaction between an α-oxocarboxylic acid and an organic hydroperoxide according to certain aspects presented herein.

Referring to FIGS. 5 and 6, in one aspect, the at least one α-oxocarboxylic acid reacts with the organic hydroperoxide via oxidative decarboxylation, thereby consuming the organic hydroperoxide, reducing the organic hydroperoxide's oxidative potential. The resulting reaction results in the oxidation of the α-oxocarboxylic acid to carbon dioxide and the corresponding carboxylic acid containing one less carbon atom, and the reduction of the organic hydroperoxide to its corresponding organic alcohol. An exemplar proposed reaction, using pyruvic acid as the α-oxocarboxylic acid and limonene-hydroperoxide as the organic hydroperoxide is depicted in FIG. 6.

In some aspects, the reaction of the at least one α-oxocarboxylic acid with the organic hydroperoxide remediates the oxidation, or oxidative damage of the formulated perfume, body care product, cosmetic product, or perfumery raw material.

In some aspects, the reduction, prevention, remediation, and/or inhibition of the oxidation of a formulated perfume, body care product, cosmetic product, or perfumery raw material may be monitored by measuring the peroxide value (POV) of the formulated perfume, body care product, cosmetic product, or perfumery raw material, wherein a reduction of the measured a POV corresponds to reduction, prevention, or inhibition of the oxidation of a formulated perfume, body care product, cosmetic product, or perfumery raw material.

As used herein, the term "peroxide value" or "POV" refers to the amount of equivalents of oxidizing potential per 1 kilogram of material. Without intending to be limited to any particular theory, the POV of a material is determined analytically. The term POV" does not refer to a chemical compound or group of compounds, but is often used loosely and interchangeably with the products of autoxidation within a sample that cause a response during a POV test. These autoxidation products differ depending upon the particular material being tested. Many classes of chemical compounds will produce a response during a POV test, including but not limited to organic and inorganic hydroperoxides, organic and inorganic peroxides, peroxyhemiacetals, peroxyhemiketals, and hydrogen peroxide itself.

By way of illustration, one POV test is an iodometric oxidation-reduction titration. All POV-responsive compounds share the property that they are capable of oxidizing the iodide ion to molecular iodine within the time period specified for the test; in fact, the iodide oxidation reaction is the basis for the test. Thus, "POV" is a numerical value that represents the molar sum total of the all the iodide-oxidizing species in a particular sample.

By way of illustration, limonene and linalool are unsaturated terpenes commonly found as major components in many essential oils. Both limonene and linalool are easily oxidized by atmospheric oxygen to form hydroperoxides. The hydroperoxides of limonene and linalool are known to be sensitizers capable of causing contact dermatitis. Consequently, limonene, and natural products containing limonene may only be used as perfumery raw materials when the recommended organic hydroperoxide level is below 20 mmol/L (or 10 mEq/L). Similarly, essential oils and isolates derived from the Pinacea family, including Pinus and Abies genera may only be used as perfumery raw materials when the recommended organic hydroperoxide level is below 10 mmol/L (or 5 mEQ/L).

The POV of a perfumery raw material may be determined by any method readily selectable by one of ordinary skill in the art. Non limiting examples include iodometric titration, high-performance liquid chromatography, and the like.

An example of a method for determining the POV of a perfumery raw material is disclosed in Calandra et al., Flavour and Fragr. J. (2015), 30, p 121-130.

Perfumery raw materials include, but are not limited to essential oils, natural extracts, and synthetic ingredients.

The POV of a formulated perfume or cosmetic product may be determined by any method readily selectable by one of ordinary skill in the art. No limiting examples include, iodometric titration, high-performance liquid chromatography, and the like.

An example of a method for determining the POV of a formulated perfume or cosmetic product is disclosed in Calandra et al., Flavour and Fragr. J. (2015), 30, p 121-130.

The POV of a formulated body care product may be determined by any method readily selectable by one of ordinary skill in the art. No limiting examples include iodometric titration, high-performance liquid chromatography, and the like.

An example of a method for determining the POV of a formulated body care product is disclosed in Calandra et al., Flavour and Fragr. J. (2015), 30, p 121-130.

Without intending to be limited to any particular theory, the methods presented herein reduce, prevent, remediate and/or inhibit the oxidation (and/or the oxidative damage) of a formulated perfume, body care product, cosmetic product, or perfumery raw material by a number of possible mechanisms. One possible mechanism is where the at least one α-oxocarboxylic acid reacts with the byproducts of the oxidation of the formulated perfume, body care product, cosmetic product, or perfumery raw material via oxidative decarboxylation. Another possible mechanism is where the at least one α-oxocarboxylic acid, or a salt thereof buffers the change in pH of the formulated perfume, body care product, cosmetic product, or perfumery raw material following exposure to the atmosphere, heat, and/or light.

One aspect presented herein provides a method,
wherein the method reduces, prevents, and/or inhibits the oxidation of a formulated perfume, body care product, cosmetic product, or perfumery raw material,
wherein the method comprises adding at least one α-oxocarboxylic acid to the formulated perfume, body care product, or perfumery raw material in an amount sufficient to reduce, prevent, and/or inhibit of the oxidation of the formulated perfume, body care product, cosmetic product, or perfumery raw material.

In some aspects, the perfumery raw material is selected from the group consisting of a synthetic ingredient, a natural product, an essential oil, and a natural extract.

In some aspects, the body care product is a skin cream.

In some aspects, the method further comprises adjusting the pH of the formulated perfume, body care product, cosmetic product, or perfumery raw material to pH 5 to pH 7.5. In some aspects, the pH of the formulated perfume, body care product, cosmetic product, or perfumery raw material is adjusted to pH 5, or pH 5.5, or pH 6, or pH 6.5, or pH 7 or pH 7.5.

In some aspects, the step of adjusting the pH comprises the addition of a buffer, such as, for example, the at least one α-oxocarboxylic acid, triethanolamine, or N-methyldiethanolamine, and the like.

One aspect presented herein, provides a method for reducing the POV of a formulated perfume, body care product, or perfumery raw material, comprising the steps of: adding at least one α-oxocarboxylic acid to the formulated perfume, body care product, or perfumery raw material having a first POV level; and mixing the at least one α-oxocarboxylic acid into the formulated perfume, body care product, or perfumery raw material for a time sufficient to reduce the first POV level to a pre-determined second lower level.

One aspect presented herein, provides a method for reducing, preventing, or inhibiting the oxidation of a formulated perfume, body care product, cosmetic product, or perfumery raw material, comprising the steps of: (a) adding at least one α-oxocarboxylic acid to the formulated perfume, body care product, or perfumery raw material having a first POV level; and (b) mixing the at least one α-oxocarboxylic acid into the formulated perfume, body care product, or perfumery raw material for a time sufficient to reduce the first POV level to a pre-determined second lower level, wherein the pre-determined second lower level is sufficient to reduce, prevent, or inhibit the oxidation of the formulated perfume, body care product, cosmetic product, or perfumery raw material.

In some aspects, the perfumery raw material is selected from the group consisting of a synthetic ingredient, a natural product, an essential oil, and a natural extract.

In one aspect, the perfumery raw material is citrus oil.

In some aspects, the body care product is a skin cream.

In some aspects, the perfumery raw material is treated prior to the incorporation into a perfume.

In some aspects, the perfumery raw material is treated after the incorporation into a perfume.

In some aspects, the pre-determined second lower level is between 5 and 20 mmol/L.

In some aspects, the method further comprises removing the excess at least one α-oxocarboxylic acid from the formulated perfume, body care product, or perfumery raw material having the pre-determined second lower POV level.

In some aspects, the excess at least one α-oxocarboxylic acid and/or the carboxylic acid byproducts are removed from the formulated perfume, body care product, or perfumery raw material via a liquid-liquid extraction.

In some aspects, the method further comprises treating the formulated perfume, body care product, or perfumery raw material after removing the at least one α-oxocarboxylic acid to reduce the acidity of the formulated perfume, body care product, or perfumery raw material.

In some aspects, the formulated perfume, body care product, or perfumery raw material is treated with a carbonate salt to reduce the acidity of the formulated perfume, body care product, or perfumery raw material.

In some aspects, the pre-determined second lower level is between 5 and 20 mmol/L. In an alternate aspect, the pre-determined second lower level is 20 mmol/L. In an alternate aspect, the pre-determined second lower level is 19 mmol/L. In an alternate aspect, the pre-determined second lower level is 18 mmol/L. In an alternate aspect, the pre-determined second lower level is 17 mmol/L. In an alternate aspect, the pre-determined second lower level is 16 mmol/L. In an alternate aspect, the pre-determined second lower level is 15 mmol/L. In an alternate aspect, the pre-determined second lower level is 14 mmol/L. In an alternate aspect, the pre-determined second lower level is 13 mmol/L. In an alternate aspect, the pre-determined second lower level is 12 mmol/L. In an alternate aspect, the pre-determined second lower level is 11 mmol/L. In an alternate aspect, the pre-determined second lower level is 10 mmol/L. In an alternate aspect, the pre-determined second lower level is 9 mmol/L. In an alternate aspect, the pre-determined second lower level is 8 mmol/L.

In an alternate aspect, the pre-determined second lower level is 7 mmol/L. In an alternate aspect, the pre-determined second lower level is 6 mmol/L. In an alternate aspect, the pre-determined second lower level is 5 mmol/L. In an alternate aspect, the pre-determined second lower level is 4 mmol/L. In an alternate aspect, the pre-determined second lower level is 3 mmol/L. In an alternate aspect, the pre-determined second lower level is 2 mmol/L. In an alternate aspect, the pre-determined second lower level is 1 mmol/L. In an alternate aspect, the pre-determined second lower level is less than 1 mmol/L.

In some aspects, the pre-determined second lower level is a 10% reduction in the POV. In an alternate aspect, the pre-determined second lower level is a 20, or 30, or 40, or 50, or 60, or 70, or 80, or 90, or 100% reduction in the POV.

In some aspects, the time sufficient to reduce the POV to a pre-determined second lower level is greater than 24 hours. In one aspect, the time sufficient to reduce the POV to a pre-determined second lower level is 24, or 23, or 22, or 21, or 20, or 19, or 18, or 17, or 16, or 15, or 14, or 13, or 12, or 11, or 10, or 9, or 8, or 7, or 6, or 5, or 4, or 3, or 2, or 1 hour(s).

In some aspects, the time sufficient to reduce the POV to a pre-determined second lower level is 60 minutes or less. In one aspect, the time sufficient to reduce the POV to a pre-determined second lower level is 60, or 50, or 40, or 30, or 20, or 10, or 9, or 8, or 7, or 6, or 5, or 4, or 3, or 2, or 1 minute.

Without intending to be limited to any particular theory, the amount of the at least one α-oxocarboxylic acid and/or the rate at which the at least one α-oxocarboxylic is added to the formulated perfume, body care product, cosmetic product, or perfumery raw material is controlled to ensure that an excess of the at least one α-oxocarboxylic does not accumulate. An excess accumulation of the at least one α-oxocarboxylic may result, for example, in acid-catalyzed damage to the formulated perfume, body care product, cosmetic product, or perfumery raw material.

The amount of the at least one α-oxocarboxylic acid that is added to the formulated perfume, body care product, cosmetic product, or perfumery raw material is dependent on several factors, including, but not limited to, the solubility of the at least one α-oxocarboxylic acid in the formulated perfume, body care product, cosmetic product, or perfumery raw material, the pKa of the at least one α-oxocarboxylic acid, the rate of reduction of the POV, the effect the α-oxocarboxylic acid has on the olfactive properties of the formulated perfume, body care product, cosmetic product, or perfumery raw material, and any combination thereof. In some aspects, the solubility of the at least one α-oxocarboxylic acid in the formulated perfume, body care product, cosmetic product, or perfumery raw material is low. By way of illustration, at the lower limit of solubility, the at least one α-oxocarboxylic acid may be practically insoluble in the formulated perfume, body care product, cosmetic product, or perfumery raw material. In contrast, at the upper limit of solubility, the at least one α-oxocarboxylic acid may be fully miscible in the formulated perfume, body care product, cosmetic product, or perfumery raw material.

Examples of aspects where the solubility of the at least one α-oxocarboxylic acid in formulated perfume, body care product, cosmetic product, or perfumery raw material is low include, but are not limited to pyruvic acid in citrus oil. In these aspects, the at least one α-oxocarboxylic acid may be added at a concentration in excess of the solubility, thus forming a two-phase system, wherein one phase consists of the at least one α-oxocarboxylic acid. Without intending to be limited to any particular theory, components of the formulated perfume, body care product, cosmetic product, or perfumery raw material may partition into the phase consisting of the at least one α-oxocarboxylic acid. Exposure of the components of the formulated perfume, body care product, cosmetic product, or perfumery raw material to the phase consisting of the at least one α-oxocarboxylic acid may result in chemical changes/damage to acid-sensitive compounds in the formulated perfume, body care product, cosmetic product, or perfumery raw material.

By way of illustration, essential oils are composed largely of terpene compounds. As a class, terpenes are generally subject to acid-catalyzed rearrangements. Consequently, exposure of the components of the formulated perfume, body care product, cosmetic product, or perfumery raw material to the phase consisting of the at least one α-oxocarboxylic acid may result in chemical changes/damage to acid-sensitive compounds in the formulated perfume, body care product, cosmetic product, or perfumery raw material, and consequently alter the organoleptic properties of the formulated perfume, body care product, cosmetic product, or perfumery raw material.

Consequently, in some aspects presented herein, the at least one α-oxocarboxylic acid is added at a rate that minimizes, or prevents the formation of the second phase consisting of the at least one α-oxocarboxylic acid. Such rate of addition may be equal to the rate of the chemical reaction that reduces the POV of the formulated perfume, body care product, cosmetic product, or perfumery raw material. In some aspects, the reduction of the POV reduces, prevents or inhibits the oxidation of the formulated perfume, body care product, cosmetic product, or perfumery raw material.

Without intending to be limited to any particular theory, addition of the α-oxocarboxylic acid at the same rate as the chemical reaction may prevent the α-oxocarboxylic acid from accumulating and thereby keep the second phase volume minimized, which will reduce partitioning of the formulated perfume, body care product, cosmetic product, or perfumery raw material into the highly acidic phase consisting of the at least one α-oxocarboxylic acid.

Alternatively, effective dispersion of the at least one α-oxocarboxylic acid in to the formulated perfume, body care product, cosmetic product, or perfumery raw material may increase the rate of the chemical reaction that reduces the POV of the formulated perfume, body care product, cosmetic product, or perfumery raw material, by increasing the surface area of contact between the two phases of the two phase system. In some aspects, the reduction of the POV reduces, prevents or inhibits the oxidation of the formulated perfume, body care product, cosmetic product, or perfumery raw material.

Examples of aspects where the solubility of the at least one α-oxocarboxylic acid in the formulated perfume, body care product, cosmetic product, or perfumery raw material is not low include, but are not limited to 2-oxo-valeric acid. Without intending to be limited to any particular theory, in aspects where the solubility of the at least one α-oxocarboxylic acid in the formulated perfume, body care product, cosmetic product, or perfumery raw material is not low may result in the formation of a single phase. Here, the added at least one α-oxocarboxylic acid is soluble in the formulated perfume, body care product, cosmetic product, or perfumery raw material being treated, and therefore will be diluted immediately upon addition. In this case, if the rate of addition is close to the rate of reaction, the at least one α-oxocarboxylic acid will also be consumed as it is being added. The concentration of the at least one α-oxocarboxylic acid will remain low, and acid-induced changes will be minimized.

In an alternate aspect, the concentration of the at least one un-reacted α-oxocarboxylic acid is minimized by using a buffer, wherein the at least one α-oxocarboxylic acid is present as a deprotonated anion.

The anionic form of the at least one α-oxocarboxylic acid will likely be unreactive toward a hydroperoxide relative to the protonated, acidic form. However, as the acidic form is consumed by reaction with hydroperoxides, the equilibrium of the at least one α-oxocarboxylic acid-base pair will quickly reestablish itself in accordance with the pKa of the at least one α-oxocarboxylic acid; the anionic form will instantly capture a proton from the media to produce more of the hydroperoxide-reactive acidic form of the at least one α-oxocarboxylic acid. In this way, the bulk acidity of the media can be maintained at a mild pH level, one that will not cause acid damage to the components of the formulated perfume, body care product, cosmetic product, or perfumery raw material. But simultaneously, there will be a relatively low but fixed level of the at least one α-oxocarboxylic acid in the reactive protonated form, replenished as soon as it is consumed from a sink of the relatively inert anionic form.

For example, using pyruvic acid for illustrative purposes only, pyruvic acid has a pKa of 2.50, buffering the formulated perfume, body care product, cosmetic product, or perfumery raw material to pH 5.5 (a difference of 3 log units), would result in $10^3$ (or 1000) times the concentration of pyruvate anion, compared to pyruvic acid (as per the Henderson-Hasselbalch equation).

In one aspect, the amount sufficient of the at least one α-oxocarboxylic acid ranges from 0.0001 to 10 weight percent of the formulated perfume, body care product, cosmetic product, or perfumery raw material. In one aspect the concentration of the at least one α-oxocarboxylic acid is 10 weight percent of the formulated perfume, body care product, cosmetic product, or perfumery raw material. Alternatively, the concentration of the at least one α-oxocarboxylic acid is 9, or 8, or 7, or 6, or 5, or 4, or 3, or 2, or 1, or 0.9, or 0.8, or 0.7, or 0.6, or 0.5, or 0.4, or 0.3, or 0.2, or 0.1, or 0.09, or 0.08, or 0.07, or 0.06, or 0.05, or 0.04, or 0.03, or 0.02, or 0.01, or 0.009, or 0.008, or 0.007, or 0.006, or 0.005, or 0.004, or 0.003, or 0.002, or 0.001, or 0.0009, or 0.0008, or 0.0007, or 0.0006, or 0.0005, or 0.0004, or 0.0003, or 0.0002, or 0.0001 weight percent of the formulated perfume, body care product, cosmetic product, or perfumery raw material.

In some aspects, the at least one α-oxocarboxylic acid is selected from the group consisting of: pyruvic acid, 2-oxovaleric acid, phenylglyoxylic acid, 2-oxobutyric acid, 2-oxo-2-furanacetic acid, α-ketoglutaric acid, 2-oxopentandioate, oxaloacetic acid, indole-3-pryruvic acid, and mixtures thereof.

In some aspects, the at least one α-oxocarboxylic acid is added to the formulated perfume, body care product, cosmetic product, or perfumery raw material as a salt. The salt may be formed by reacting the at least one α-oxocarboxylic acid with an organic base.

In the aspects where the at least one α-oxocarboxylic acid is a mono-acid, the resultant salt may be a mono-salt. In the aspects where the at least one α-oxocarboxylic acid is a di-acid, the resultant salt may be a mono-salt, or a di-salt.

Examples of suitable organic bases include, but are not limited to the organic bases described in Examples 7-11 below, polymeric amines, polyetylamines, and the like.

Alternatively, the salt may be formed by reacting the at least one α-oxocarboxylic acid with a cation selected from the group consisting of: $Na^+$, $K^+$, $Mg^{2+}$, and $Ca^{2+}$.

An example of a diammonium salt includes the diammonium salt formed by reacting the at least one α-oxocarboxylic acid with N-methyl diethanolamine In some aspects, the molar ratio of the at least one α-oxocarboxylic acid to N-methyl diethanolamine may be 1:2, or 1:1, or 2:1.

In some aspects, the at least one α-oxocarboxylic acid may be reacted with N-methyl diethanolamine by dissolving the at least one α-oxocarboxylic acid in a solvent, such as, for example, acetone, and adding N-methyl diethanolamine to the solution. The resultant opaque, white emulsion may then be vortexed, during which time a second phase may coalesce. The mixture may then be placed in a freezer for at least 30 minutes, causing the bottom phase to thicken to a waxy solid. While still cold, the top layer may then be easily removed via decantation and discarded. Residual acetone may be removed from the bottom product layer via a stream of nitrogen followed by treatment in a vacuum oven at room temperature, thereby resulting in a faint yellow, highly viscous oil at room temperature comprising the diammonium salt.

Other compounds suitable to form the diammonium salt via reaction with the at least one α-oxocarboxylic acid include, 2-(dimethylamino)ethanol, and N, N-dimethyldodecylamine.

The α-oxocarboxylic acid can be added directly to the formulated perfume, body care product, cosmetic product, or perfumery raw material, or, alternatively, the α-oxocarboxylic acid can be diluted prior to addition to the formulated perfume, body care product, cosmetic product, or perfumery raw material. Any diluent that may be used in perfumery may be used. Suitable diluents include, but are not limited to isopropanol, ethanol, diglyme, triethyleneglycol, and the like. The α-oxocarboxylic acid may be diluted 1:1, or 1:2, or 1:3, or 1:4, or more with the diluent.

Without intending to be limited by any particular theory, the choice of diluent may also influence the amount of the at least one α-oxocarboxylic acid that may be added to the formulated perfume, body care product, cosmetic product, or perfumery raw material. In addition, the choice of diluent may also influence the rate at which the at least one α-oxocarboxylic acid that is be added to the formulated perfume, body care product, cosmetic product, or perfumery raw material. For example, by way of illustration, using pyruvic acid as the at least one α-oxocarboxylic acid, and ethanol as the solvent, the pyruvic acid must be added in an amount, and/or a at a rate that minimizes the formation of an ester with the ethanol.

The at least one α-oxocarboxylic acid can be added to any volume of the formulated perfume, body care product, cosmetic product, or perfumery raw material. For example, the at least one α-oxocarboxylic acid can be added can be added to 1000 ml of formulated perfume, body care product, cosmetic product, or perfumery raw material, or 900, or 800, or 700, or 600, or 500, or 400, or 300, or 200, or 100, or 90, or 80, or 70, or 60, or 50, or 40, or 30, or 20, or 10, or 9, or 8, or 7, or 6, or 5, or 4, or 3, or 2, or 1 ml of formulated perfume, body care product, cosmetic product, or perfumery raw material.

In one aspect, the at least one α-oxocarboxylic acid may be added to the formulated perfume, body care product, cosmetic product, or perfumery raw material over 80 minutes. Alternatively, the at least one α-oxocarboxylic acid may be added to the formulated perfume, body care product, cosmetic product, or perfumery raw material over 70, or 60, or 50, or 40, or 30, or 20, or 10, or 9, or 8, or 7, or 6, or 5, or 4, or 3, or 2, or 1 minute(s).

In one aspect, the at least one α-oxocarboxylic acid is added to the formulated perfume, body care product, cosmetic product, or perfumery raw material at a rate of 0.25 ml per minute. In some aspects, the rate of addition is greater than 0.25 ml per minute. In some aspects, the rate of addition is less than 0.25 ml per minute.

Figure 8:
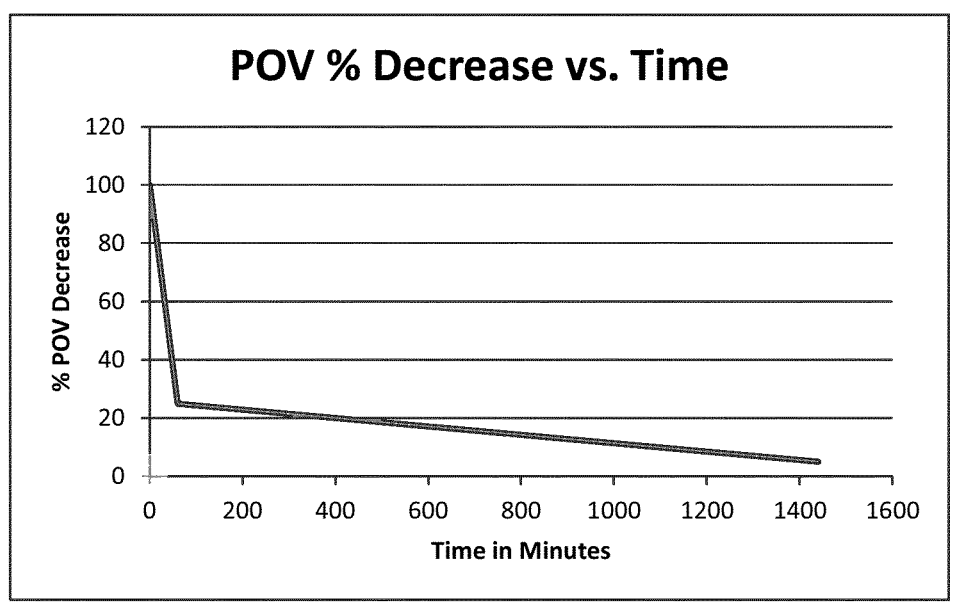
FIG. 8 shows a representation of the rate of reduction of POV in a perfumery raw material according to certain aspects presented herein.
Figure 9:
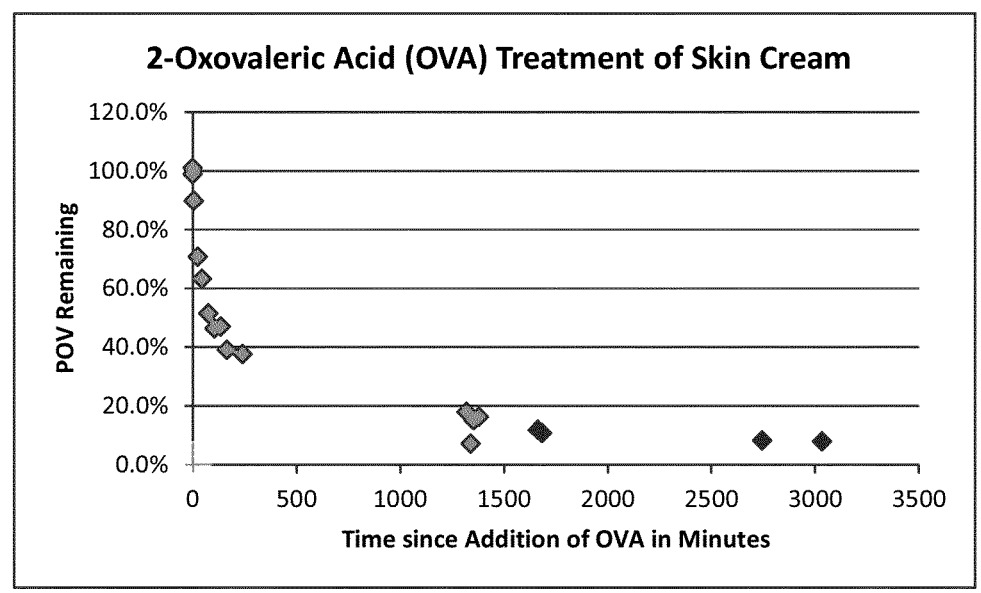
FIG. 9 shows POV of a skin cream by a method according to certain aspects presented herein.
Figure 10:
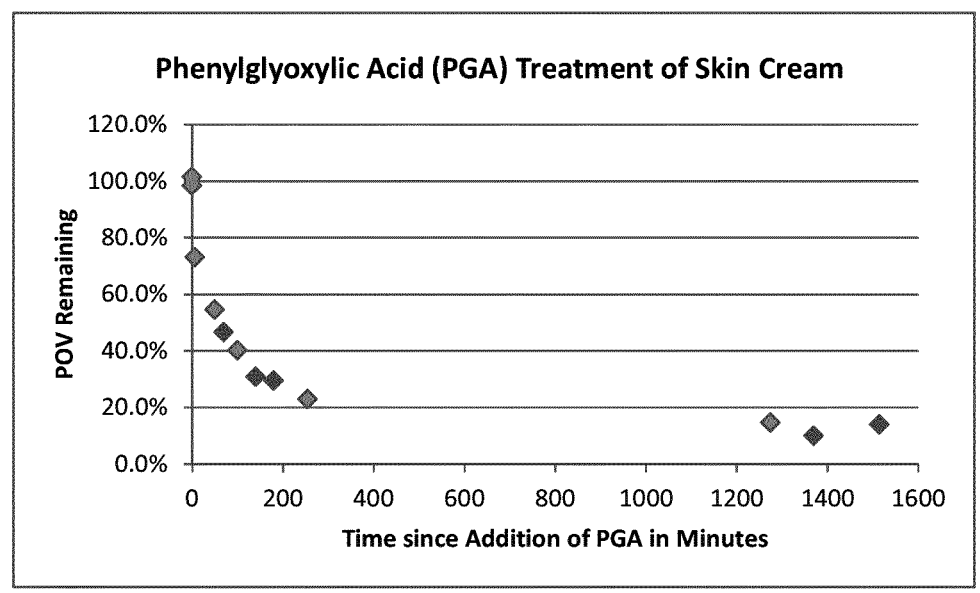
FIG. 10 shows POV of a skin cream by a method according to certain aspects presented herein.

In some aspects, the rate at which the at least one α-oxocarboxylic acid is added to the formulated perfume, body care product, cosmetic product, or perfumery raw material is constant. In some aspects, the rate at which the at least one α-oxocarboxylic acid is added to the formulated perfume, body care product, cosmetic product, or perfumery raw material varies. In one aspect, the α-oxocarboxylic acid is added to the formulated perfume, body care product, cosmetic product, or perfumery raw material at a rate equal to the rate at which the α-oxocarboxylic acid is oxidized. In some aspects, the rate at which the at least one α-oxocarboxylic acid is oxidized may be determined by measuring the POV in the treated formulated perfume, body care product, cosmetic product, or perfumery raw material. Referring to FIGS. 8 to 10, by way of illustration, the rate of reduction of POV may have a first rate, which is greater than a second rate. In the aspect illustrated, the duration of the first rate is less than the duration of the second rate.

In an alternate aspect, the at least one α-oxocarboxylic acid may be added, and subsequently quenched after a period of time. The at least one α-oxocarboxylic acid may be quenched 80 minutes after addition to the substance. Alternatively, the α-oxocarboxylic acid may be quenched 70, or 60, or 50, or 40, or 30, or 20, or 10, or 9, or 8, or 7, or 6, or 5, or 4, or 3, or 2, or 1 minute(s) after addition to the substance.

The quenching may be performed by the addition of $NaNCO_3$, or similar compounds.

In some aspects, the method further comprises removing the excess at least one α-oxocarboxylic acid from the formulated perfume, body care product, cosmetic product, or perfumery raw material.

In some aspects, the excess at least one α-oxocarboxylic acid is removed from the formulated perfume, body care product, cosmetic product, or perfumery raw material via a liquid-liquid extraction.

In some aspects, other byproducts of the reaction that reduces, prevents, and/or inhibits the oxidation of the formulated perfume, body care product, cosmetic product, or perfumery raw material to the pre-determined second lower level are also removed by the liquid-liquid extraction. All byproducts, or, alternatively, a portion of the byproducts may be removed.

In some aspects, the method further comprises treating the formulated perfume, body care product, cosmetic product, or perfumery raw material after removing the excess α-oxocarboxylic acid to reduce the acidity of the substance. In some aspects, the treatment comprises the addition of a base to form buffer. Bases include, for example, triethanolamine, or N-methyldiethanolamine, and the like.

In some aspects, the substance is treated with a carbonate salt to reduce the acidity of the formulated perfume, body care product, cosmetic product, or perfumery raw material.

In one aspect, the amount sufficient of the at least one α-oxocarboxylic acid is sufficient to reduce, prevent, and/or inhibit a change in the pH of the formulated perfume, body care product, cosmetic product, or perfumery raw material.

In some aspects, the reduction, prevention, and/or inhibition of the oxidation reduces, prevents, and/or inhibits a discoloration of the formulated perfume, body care product, cosmetic product, or perfumery raw material.

In some aspects, the reduction, prevention, and/or inhibition of the change in the pH reduces, prevents, and/or inhibits a discoloration of the formulated perfume, body care product, cosmetic product, or perfumery raw material.

Discoloration of the formulated perfume, body care product, cosmetic product, or perfumery raw material may be determined by any suitable method, such as, for example, measuring the absorbance of the formulated perfume, body care product, cosmetic product, or perfumery raw material at a specific wavelength of light, such as, for example, 530 nm.

In some aspects, the reduction, prevention, and/or inhibition of the oxidation increases, enhances, and/or improves the stability and/or shelf life of the formulated perfume, body care product, cosmetic product, or perfumery raw material.

In some aspects, the reduction, prevention, and/or inhibition of the change in the pH increases, enhances, and/or improves the stability and/or shelf life of the formulated perfume, body care product, cosmetic product, or perfumery raw material.

In some aspects, the method further comprises adding at least one stabilizer to the formulated perfume, body care product, cosmetic product, or perfumery raw material. Suitable stabilizers include, for example, UV filters, quenchers, buffers, and the like.

In some aspects, the at least one stabilizer is selected from the group consisting of: butyl methoxydibenzoyl methane, ethylhexyl methoxycinnamate, ethylhexyl salicylate, tris(tetramethylhydroxypiperidinol) citrate, and mixtures thereof.

Other stabilizers suitable for use in the various aspects presented herein include, but are not limited to benzophenone-3, benzophenone-4, homosalate, octocrylene, and mixtures thereof.

In some aspects, the at least one stabilizer is added at a concentration from 0.01 to 2 wt % of the formulated perfume, body care product, cosmetic product, or perfumery raw material. In some aspects, the concentration of the at least one stabilizer is 2 wt % of the formulated perfume, body care product, cosmetic product, or perfumery raw material. Alternatively, the concentration of the at least one stabilizer is 1.9, or 1.8, or 1.7, or 1.6, or 1.5, or 1.4, or 1.3, or 1.2, or 1.1, or 1, or 0.9, or 0.8, or 0.7, or 0.6, or 0.5, or 0.4, or 0.3, or 0.2, or 0.1, or 0.09, or 0.08, or 0.07, or 0.06, or 0.05, or 0.04, or 0.03, or 0.02, or 0.01 wt % of the formulated perfume, body care product, cosmetic product, or perfumery raw material.

In some aspects, the at least one α-oxocarboxylic acid may reduce the amount of the at least one stabilizer that is added to the formulated perfume, body care product, cosmetic product, or perfumery raw material.

In some aspects, the at least one stabilizer may reduce the amount of the at least one α-oxocarboxylic acid that is added to the formulated perfume, body care product, cosmetic product, or perfumery raw material.

In some aspects, the method is performed at room temperature. In an alternate aspect, the method is performed at a temperature ranging from −20 degrees Celsius to 78 degrees Celsius.

In some aspects, the perfumery raw material is selected from the group consisting of a synthetic ingredient, a natural product, an essential oil, and a natural extract.

In some aspects, the perfumery raw material is citrus oil.

In some aspects, the perfumery raw material is treated prior to the incorporation into a perfume.

In some aspects, the perfumery raw material is treated after the incorporation into a perfume.

In some aspects, the at least one α-oxocarboxylic acid has FEMA-GRAS status.

In some aspects, the method for reducing the POV of formulated perfume, body care product, or perfumery raw material, comprises the steps of:
 a) introducing the formulated perfume, body care product, or perfumery raw material into a reaction vessel, wherein the formulated perfume, body care product, or perfumery raw material is under an inert gas, such as, for example, argon;
 b) introducing the at least one α-oxocarboxylic acid to the formulated perfume, body care product, or perfumery raw material at a rate of 0.25 ml per minute, wherein the α-oxocarboxylic acid is diluted 1:4 with a diluent, wherein the at least one α-oxocarboxylic acid to the formulated perfume, body care product, or perfumery raw material is constantly stirred during the introduction;
 c) introducing water and anhydrous sodium carbonate to the mixture and allowing the reaction to continue until there is no longer any visible evolution of $CO_2$; and
 d) discarding the aqueous layer, thereby obtaining a formulated perfume, body care product, or perfumery raw material with a POV having a pre-determined second lower level.

An example of a method according to the aspect described above can be found in Examples 1 to 4 below.

In some aspects, the second phase of the at least one α-oxocarboxylic acid in the formulated perfume, body care product, or perfumery raw material is a "leave-in" composition of the at least one α-oxocarboxylic acid. Without intending to be limited to any particular theory, the amount at least one α-oxocarboxylic acid present in the two phases is in equilibrium, and the reduction of POV may result in the at least one α-oxocarboxylic acid moving from the phase consisting of at least one α-oxocarboxylic acid, into the phase containing the formulated perfume, body care product, or perfumery raw material. One example of this aspect is described in Example 5 below.

In some aspects, the "leave-in" composition of the at least one α-oxocarboxylic acid comprises a single phase composition with the formulated perfume, body care product, or perfumery raw material. In these aspects, the composition further comprises a buffer, wherein the pH is configured to maintain the majority of the at least one α-oxocarboxylic acid present in a non-protonated form, wherein the non-protonated form is incapable of reacting with the chemical species that contribute to the POV of the composition (including peroxides, organic hydroperoxides, peroxyhemiacetals). Without intending to be limited to any particular theory, the amount of the at least one α-oxocarboxylic acid present in non-protonated form is in equilibrium with an amount of amount of the at least one α-oxocarboxylic acid present in protonated form, and the reduction of POV may result in the at least one α-oxocarboxylic acid moving from the non-protonated from to the protonated form. One example of this aspect is described in Example 4 below.

In these instances, the "leave-in" compositions of the at least one α-oxocarboxylic acid is capable of reducing POV for a prolonged period of time.

Accordingly, one aspect presented herein, provides a composition comprising: (a) a formulated perfume, body care product, or perfumery raw material, and (b) at least one α-oxocarboxylic acid, wherein the at least one α-oxocarboxylic acid is present in the composition in an amount sufficient to decrease the POV from a first level to a pre-determined second lower level.

In one aspect, the at least one α-oxocarboxylic acid is present in the composition in an amount sufficient to prevent the pre-determined second lower level from changing with time. The time may be hours, days, weeks, or longer.

An example of a composition according to the aspect described above can be found in Example 5 below.

One aspect presented herein provides a composition comprising a formulated perfume, body care product, cosmetic product, or perfumery raw material and at least one α-oxocarboxylic acid, wherein the at least one α-oxocarboxylic acid is in present in the composition in an amount sufficient to reduce, prevent, and/or inhibit the oxidation of the formulated perfume, body care product, cosmetic product, or perfumery raw material.

In some aspects, the composition further comprises at least one stabilizer.

In some aspects, the concentration of the at least one stabilizer in the composition is from 0.01 to 1 wt %.

In some aspects, the at least one stabilizer is selected from the group consisting of: butyl methoxydibenzoyl methane, ethylhexyl methoxycinnamate, ethylhexyl salicylate, tris(tetramethylhydroxypiperidinol) citrate, and mixtures thereof.

In some aspects, the at least one α-oxocarboxylic acid is selected from the group consisting of: pyruvic acid, 2-oxovaleric acid, phenylglyoxylic acid, 2-oxobutyric acid, 2-oxo-2-furanacetic acid, α-ketoglutaric acid, 2-oxopentandioate, oxaloacetic acid, indole-3-pryruvic acid, and mixtures thereof.

In some aspects, the amount sufficient of the at least one α-oxocarboxylic acid is from 0.0001 to 10 weight percent of the formulated perfume, body care product, cosmetic product, or perfumery raw material.

In some aspects, the at least one α-oxocarboxylic acid is added to the formulated perfume, body care product, cosmetic product, or perfumery raw material as a diammonium salt.

In some asoects, the formulated perfume, body care product, cosmetic product, or perfumery raw material further comprises a dye. Examples of dyes sutable for use in the various aspects described herein include, but are not limited to Blue 1, Red 4, Red 33, Yellow 5, Yellow 6, Orange 4, and the like.

Non-limiting examples of suitable formulated perfumes, body care products, or cosmetic products include:
- a perfume, such as a fine perfume, an Eau de Toilette, a cologne or an after-shave lotion;
- a fabric care product, such as a liquid detergent, a powder detergent, detergent tablets, a detergent bar, a detergent paste, a detergent pouch, a liquid fabric softener, fabric softener sheets, a fabric scent booster, a laundry pre-treatment, a fabric refresher, an ironing water, a laundry bleach, a carpet powder or a carpet cleaner;
- a hair care product, such as a shampoo, a hair conditioner, a hair cream, a hair oil, a hair styling product (such as a spray, mousse or gel), a hair coloration product or a hair permanent wave product;
- a skin care product, such as a face cream, a face lotion, a shaving product (such as a foam, cream, gel or oil), a body and/or hand product (such as a lotion, cream, gel or oil), a skin firming product, a depilatory, a talcum powder, a foot care cream or lotion, baby wipes, cleansing wipes, moisturizer wipes, a sun-protection product (such as a spray, lotion, cream or oil), an after-sun lotion, or a self-tanning product;
- a body deodorant or antiperspirant product, such as a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream;
- a skin-cleansing product, such as a soap bar, a shower gel, a liquid hand soap, a bath foam or an intimate wash product;
- an air freshening product, such as an air freshener spray, a gel air freshener, a liquid-wick air freshener, a solid air freshener comprising a porous substrate (such as a paper or card blotter, a porous ceramic, or a porous plastic), a liquid or gel air freshener comprising a permeable membrane, an electrically operated air freshener, and a dual purpose air freshener/disinfectant spray; and/or
- a surface care product, such as an all-purpose cleaner, a furniture polish, a wood floor cleaner, a window cleaner, a hand dishwashing product (such as a liquid, gel or paste), a machine dishwashing product (such as a powder, liquid, gel, tablet or sachet), a toilet bowl cleaning liquid, an in-cistern toilet cleaner, a toilet rim block, or a toilet rim liquid; a pet-litter.

The present invention is best illustrated but is not limited to the following examples.

EXAMPLES

Example 1

Reduction of POV in Citrus Oil According to One Aspect Presented Herein Using Pyruvic Acid 50 mL of mixed citrus oils (orange, lemon, lime, mandarin, bergamot, and tangerine) were placed in a 100 round bottom flask at room temperature, along with a stir bar and an argon gas blanket.

A 4:1 v/v isopropanol/pyruvic acid solution was made. 20 mL of this pyruvic acid solution was dripped into the stirred citrus oils at a rate of 0.25 mL/minute via the use of a syringe pump.

When the addition was complete, 10 mL of water and 100 mg of anhydrous sodium carbonate was added to the flask, and the stirring was maintained. When the visible evolution of $CO_2$ had stopped (about 2-4 minutes), the aqueous layer was removed with a pipette and discarded. POV measurements were made on the mixed citrus oil before and after the pyruvic acid treatment.

POV before treatment was 27.261 mEq/L, and the POV after treatment was 4.786 mEq./L. This was about an 82% reduction in POV.

Example 2

Reduction of POV in Limonene According to One Aspect Presented Herein Using 2-Oxo-Valeric Acid 10 mL of autoxidized limonene was placed in a 30 mL glass vial at room temperature, along with a stir bar and an argon gas blanket. 100 µL of 2-oxovaleric acid was added. The vial was shaken once and allowed to stand for 50 minutes. No further treatment was done prior to the POV testing. POV measurements were made on the limonene before and after the 2-oxovaleric acid treatment. POV before treatment was 65.97 mEq./L, and POV after treatment was 17.21 mEq./L. This was an approximately 74% reduction in POV.

Example 3

Reduction of POV in Limonene According to One Aspect Presented Herein Using 2-Oxo-Butyric Acid 20 mL of autoxidized limonene was placed in a 30 mL glass vial at room temperature, along with a stir bar and an argon gas blanket. 250 µL of 2-oxobutyric acid was added. The vial was shaken once and allowed to stand, while being monitored for POV value as a function of time. The data collected is shown in the table below.

| Time (in min.) since addition of 2-oxobutryric acid | POV (in mEq/L) | POV reduction (in %) |
| --- | --- | --- |
| Untreated | 66.245 | 0.0 |
| 3 | 43.680 | 34.1 |
| 20 | 22.140 | 66.6 |
| 35 | 22.681 | 65.8 |
| 44 | 19.968 | 69.9 |
| 66 | 21.406 | 67.7 |
| 116 | 19.576 | 70.4 |
| 176 | 20.964 | 68.4 |

The results showed an initial rapid reduction in POV, followed by decline in the rate of POV reduction. This may be due to reagent depletion, but the loss of POV is not sufficient to fully account on a molar basis for all of the added 2-oxobutyric acid. It may be that some hydroperoxides are destroyed very quickly, and other oxidants are destroyed much more slowly. When an additional 500 µL of 2-oxobutyric acid was added, and the sample allowed to stand for an additional 24 hours, the measured POV was 8.577 mEq./L (87.1% total reduction).

Example 4

Reduction of POV in Limonene According to One Aspect Presented Herein Using 2-Phenylglyoxylic Acid 20 mL of autoxidized limonene was placed in a 30 mL glass vial at room temperature, along with a stir bar and an argon gas blanket. 200 mg of phenylglyoxylic acid was added, which dissolved. The vial was shaken once and allowed to stand, while being monitored for POV value as a function of time. The data collected is shown in the table below.

| Time (in min.) since addition of phenylglyoxylic acid | POV (in mEq/L) | POV reduction (in %) |
|---|---|---|
| Untreated | 44.795 | 0.0 |
| 40 | 37.035 | 17.3 |
| 150 | 34.086 | 23.9 |
| 190 | 29.963 | 33.1 |
| 2880 (48 hrs) | 17.265 | 61.5 |

Example 5

Reduction of POV in Limonene According to One Aspect Presented Herein Using 2-Oxo-2-Furanacetic Acid 20 mL of mixed citrus oil was placed in a 30 mL glass vial at room temperature, along with a stir bar and an argon gas blanket. 400 mg of α-oxo-2-furanacetic acid was added. The vial was shaken once and allowed to stand, while being monitored for POV value as a function of time. The majority of the added α-oxo-2-furanacetic acid did not dissolve, so the limited solubility of the acid will likely act as a controlled release mechanism; as the α-oxo-2-furanacetic acid in solution is consumed by hydroperoxides, more will likely dissolve in accordance will the solubility constant. In this way, the undissolved solid acts as a sink to maintain a steady, low concentration of α-oxo-2-furanacetic acid dissolved in the mixed citrus oil.

In this case, because the time between measurements was relatively long (days instead of minutes), there is the possibility that the untreated mixed citrus oil will oxidize further during the course of the experiment. Therefore, the POV of the treated oil was still compared with the POV of the untreated oil, but the measurement of the untreated oil was re-determined at each time point (rather than just a single, initial value being used). The data collected is shown in the table below.

| Time (in days) since addition of α-Oxo-2-furanacetic acid | Untreated POV (in mEq/L) | Treated POV (in mEq/L) | POV reduction (in %) |
|---|---|---|---|
| Untreated | 20.593 | 20.593 | 0.0 |
| 2 | 25.366 | 18.566 | 26.8 |
| 4 | 28.581 | 17.193 | 39.8 |
| 44 | 29.119 | 1.106 | 96.2 |

Example 6

Reduction of POV in a Skin Cream Formulation According to One Aspect Presented Herein Using 2-Oxovaleric Acid or Phenylglyoxylic Acid A skin cream formulation comprising of 0.5 parts cetylstearyl alcohol, 6.0 parts wool wax alcohol, and 93.5 parts white petroleum jelly was created as per the German Pharmacopoeia DAB 2008.

The skin cream was divided into two separate preparations. A highly oxidized limonene sample was added to both preparations, with the first preparation receiving a concentration of oxidized limonene approximately one third of the concentration of the oxidized limonene in the second preparation. Analysis of the oxidized limonene sample showed the sample to contain a mixture of limonene hydroperoxide isomers.

The initial POV of both the first and second skin cream preparations was taken, prior to treatment with 2-oxovaleric acid or phenylglyoxylic acid as follows: 2-oxovaleric acid (second preparation), or phenylglyoxylic acid (first preparation) was thoroughly blended into the skin cream preparations. The POV of the preparations were measured, during addition of the 2-oxovaleric acid. After addition of the 2-oxovaleric acid or phenylglyoxylic acid, the treated preparations were allowed to stand at room temperature. The POV data obtained was corrected for the exact weight of the aliquot of cream titrated at each individual time point, and normalized as a percentage to the starting POV.

The second preparation, containing the highest amount of the oxidized limonene sample was treated with approximately 2.3% w/w 2-oxovaleric acid. The results are shown below in FIG. 9.

The first preparation, containing the lowest amount of the oxidized limonene sample was treated with approximately 3.9% w/w 2-phenylglyoxylic acid. The results are shown below in FIG. 10.

Example 7

Formation of a Diammonium Salt via the Reaction of α-Ketoglutaric Acid (CAS #328-50-7) and N-Methyl Diethanolamine (NMDEA, CAS #105-59-9) in a 1:2 Molar Ratio 1.461 g (0.01 moles) of α-ketoglutaric acid was dissolved in 10 mL of dry acetone to give a clear solution. This solution was added as one portion to 2.384 g (0.02 moles) of neat NMDEA. The opaque, white emulsion was vortexed vigorously for 3-4 minutes, during which time a second phase had coalesced. The mixture was placed in a freezer for at least 30 minutes, causing the bottom phase to thicken to a waxy solid. While still cold, the top layer was easily removed via decantation or pipet, and discarded. Residual acetone was removed from the bottom, product layer via a stream of nitrogen followed by treatment in a vacuum oven at room temperature. This resulted in a clear, faint yellow, highly viscous oil at room temperature containing the diammonium salt (AKG-DiNMDEA salt).

A model perfume was made using 90/10 v/v ethanol/water as a solvent, and a mixture of orange, grapefruit, and bergamot oils as the perfume oil. The mixed citrus oil was loaded into the solvent at approximately 19.4% v/v (6 mL oil into 25 mL solvent). Approximately 400 mg (2.0% w/v) of the AKG-DiNMDEA salt was dissolved in 20 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Minutes | POV of Treated Perfume | POV of Untreated Perfume |
|---|---|---|
| 0.0 | 12.39 mmol/L | 12.39 mmol/L |
| 70 | 8.07 | — |
| 90 | 6.16 | — |

-continued

| Time in Minutes | POV of Treated Perfume | POV of Untreated Perfume |
|---|---|---|
| 1150 | 1.38 | — |
| 1165 | 1.06 | — |
| 1180 | 0.85 | — |
| 1195, 1210 | — | 12.31, 13.60 |
| 1220 | 0.78 | — |
| 1400 | — | 13.38 |
| 1420 | 0.77 | — |
| 1440 (24 hours) | 0.79 | — |

These data show a reduction in the POV of approximately 94%, 24 hours after addition of the AKG-DiNMDEA salt.

Example 8

Formation of a Diammonium Salt via the Reaction of α-Ketoglutaric Acid (CAS #328-50-7) and N,N-dimethyldodeclyamine (DiMeC12A, CAS #112-18-5) in a 1:2 Molar Ratio 1.461 g (0.01 moles) of α-ketoglutaric acid was dissolved in 6 mL of dry acetone. This solution was added dropwise with stirring over the course of 1-2 minutes to a separate solution of 4.268 g (0.02 moles) of N, N dimethyldodecylamine in 6 mL of dry acetone. No visible indication of reaction was seen except that the combined solution warmed up to about 35-40° C. The mixture was shaken briefly but vigorously, and cooled in a freezer for 30 minutes. Even when cold, still no precipitation of product occurred, but when the mixture was shaken again, the entire mass almost instantly solidified into a solid, white, waxy substance. This solid was warmed up to 30-35° C. to re-liquify the product so that entrapped acetone could be removed via a stream of nitrogen followed by treatment in a vacuum oven at room temperature. This gave a white, waxy solid containing the diammonium salt (AKG-DiMeC12A salt).

A model perfume was made using 90/10 v/v ethanol/water as a solvent, and a mixture of orange, grapefruit, and bergamot oils as the perfume oil. The mixed citrus oil was loaded into the solvent at approximately 19.4% v/v (6 mL oil into 25 mL solvent). Approximately 400 mg (2.0% w/v) of the AKG-DiMeC12A salt was dissolved in 20 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Minutes | POV of Treated Perfume | POV of Untreated Perfume |
|---|---|---|
| 0.0 | 12.74 mmol/L | 12.74 mmol/L |
| 35 | 8.31 | — |
| 45 | 8.35 | — |
| 70 | 6.77 | — |
| 130 | 6.54 | — |
| 145 | 5.82 | — |
| 180 | 4.89 | — |
| 210 | 4.51 | — |
| 240 (4 hours) | 4.15 | — |
| 270 | 3.49 | — |
| 4320 (3 days, 72 hours) | 0.0 indistinguishable from blank | 14.43 |

Example 9

Formation of a Diammonium Salt via the Reaction of α-ketoglutaric acid and (CAS #328-50-7) and 2-(dimethylamino(ethanol) (Deanol, CAS #108-01-0) in a 1:2 Molar Ratio 1.461 g (0.01 moles) of α-ketoglutaric acid was dissolved in 10 mL of dry acetone to give a clear solution. This solution was added over the course of 1-2 minutes with stirring to 1.783 g (0.02 moles) of neat 2 dimethylaminoethanol ("Deanol"). The opaque, white emulsion was vortexed vigorously for a minute, during which time a second phase had coalesced. The mixture was placed in a freezer overnight, causing the bottom phase to thicken to extremely viscous, hazy oil. While still cold, the top layer was easily removed via decantation or pipet, and discarded. Residual acetone was removed from the bottom product layer via a stream of nitrogen followed by treatment in a vacuum oven at room temperature. This produced clear, colorless, viscous oil at room temperature containing the diammonium salt (AKG DiDeanol salt).

A model perfume was made using 90/10 v/v ethanol/water as a solvent, and a mixture of orange, grapefruit, and bergamot oils as the perfume oil. The mixed citrus oil was loaded into the solvent at approximately 19.4% v/v (6 mL oil into 25 mL solvent). Approximately 200 mg (1.0% w/v) of the AKG DiDeanol salt was dissolved in 20 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Minutes | POV Treated Perfume | POV Untreated Perfume |
|---|---|---|
| 45 | — | 11.73 mmol/L |
| 60 | 5.95 mmol/L | — |
| 75 | 5.66 | — |
| 115 | 4.96 | — |
| 195 | 3.20 | — |
| 210 | 3.08 | — |
| 270 | — | 12.25 |
| 300 (5 hours) | 2.31 | — |
| 370 | 1.73 | — |
| 380 | 1.72 | — |
| 390 | — | 11.70 |
| 1440 (24 hours) | 0.0 indistinguishable from blank | 11.79 |

Example 10

Formation of a Diammonium Salt via the Reaction of Pyruvic Acid (CAS #328-50-7) and N-methyl diethanolamine (NMDEA, CAS #105-59-9) in a 1:1 Molar Ratio 2.642 g (0.03 moles) of pyruvic acid was dissolved in 5 mL of dry acetone to give a clear solution. This solution was added dropwise with stirring over the course of 1-2 minutes to a second solution made from 3.575 g (0.03 moles) of NMDEA and 5 mL of dry acetone. The resulting mixture became warm (approximately 35-45° C.) and hazy as the acid solution was added. The milky emulsion was vortexed vigorously for a minute, during which time a second phase had coalesced. The mixture was placed in a freezer for at least 1 hour, causing the bottom phase to increase significantly in viscosity, but not solidify. While still cold, the top layer was easily removed via decantation or pipet, and discarded. Residual acetone was removed from the bottom product layer via a stream of nitrogen followed by treatment in a vacuum oven at room temperature. This gave clear, golden colored, highly viscous oil at room temperature containing the diammonium salt (PA-NMDEA salt).

A model perfume was made using 90/10 v/v ethanol/water as a solvent, and a mixture of lime, orange, grapefruit, and bergamot oils as the perfume oil. The mixed citrus oil was loaded into the solvent at approximately 16.7% v/v (40 mL oil into 200 mL solvent, 240 mL total perfume). Approximately 150 mg (1.0% w/v) of the PA-NMDEA salt was dissolved in 15 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Hours | POV Treated Perfume | POV Untreated Perfume |
| --- | --- | --- |
| 0.0 | — | 5.55 mmol/L |
| 1.8 | 3.48 mmol/L | — |
| 71.5 | 1.01 | — |
| 72.5 | — | 6.66 |
| 73.3 | 0.58 | — |
| 74.7 | — | 6.58 |

These data suggest that the PA-NMDEA was depleted at the 73.3 hour mark, because the POV of the sample never went any lower after that, even at extended reaction times. This represents >90% reduction in POV; the average untreated oil after 3 days was (6.66+6.58)/2=6.62 mmol/L, so 0.58/6.62×100 =8.76% remaining, or 91.2% reduction in POV).

Example 11

Formation of an Ammonium Salt via the Reaction of Phenylglyoxylic Acid (PhGA, CAS #611-73-4) and N-methyl diethanolamine (NMDEA, CAS #105-59-9) in a 1:1 Molar Ratio 1.501 g (0.01 moles) of PhGA was dissolved in 5 mL of dry acetone to give a clear solution. This solution was added in one portion to a second solution made from 1.192 g (0.01 moles) of NMDEA and 5 mL of dry acetone. The resulting mixture became warm (approximately 30-35° C.) and turned pale yellow in color, but no haze or precipitate formed. The solution was vortexed vigorously for a minute, and placed in a freezer for 30 minutes. Still no precipitate or second layer formed, but the solution was apparently supersaturated. An attempt was made to remove the solvent acetone via a stream of nitrogen, but almost instantly as the nitrogen stream touched the solution, a thick paste of white crystalline material formed. The crystals began to re-dissolve back into the acetone as the mixture warmed to room temperature. The product was re-frozen, causing re-precipitation of the highly crystalline product, and the supernatant acetone was removed while still cold via pipet as much as possible. Residual acetone was then removed under a stream of nitrogen to give pure white, needle shaped crystals. The crystalline product containing the diammonium salt (PhGA-NMDEA salt) was extremely hygroscopic, and would liquefy very rapidly if exposed to ambient atmosphere; the white mass of needles had to be kept under vacuum or a rigorous nitrogen blanket to remain crystalline. A weight/yield was not obtained due to the hygroscopicity.

A model perfume was made using 90/10 v/v ethanol/water as a solvent, and a mixture of lime, orange, grapefruit, and bergamot oils as the perfume oil. The mixed citrus oil was loaded into the solvent at approximately 16.7% v/v (40 mL oil into 200 mL solvent, 240 mL total perfume). Approximately 150 mg (1.0% w/v) of the PhGA-NMDEA salt was dissolved in 15 mL of the mixed citrus perfume, and POV measurements were taken as a function of time after the addition. An untreated perfume sample was handled similarly to the treated perfume and also tested, because the POV can rise rapidly with handling of the sample (opening the bottle, agitation, etc.). The results are shown in the table below.

| Time in Hours | POV Treated Perfume | POV Untreated Perfume |
| --- | --- | --- |
| 0.0 | — | 5.55 mmol/L |
| 1.8 | 4.87 mmol/L | — |
| 71.5 (~3 days) | 4.61 | — |
| 72.5 | — | 6.66 |
| 73.3 | 4.18 | — |
| 74.7 | — | 6.58 |
| 243 (~10 days) | 2.62 | 8.37 |

These data suggest that while the phenylglyoxylic acid moiety does work to lower the POV in the model perfume, it is less reactive than the non-aryl pyruvates studied. This difference in reactivity may be useful in some circumstances.

Example 12

Figure 7:
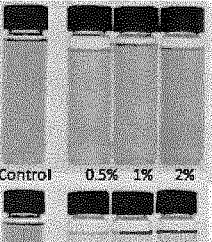
FIG. 7 shows the effect of compositions according to certain aspects presented herein on the light-induced changes in the visual appearance of a perfuming composition.
Figure 7:

Prevention of the Light-Induced Oxidation of a Solution Containing a Perfume Raw Material According to Some Aspects Presented Herein In a first series of experiments, the effect of the concentration of the perfume raw material vanillin on the stability of the dye Red 33 over time was investigated. Test solutions were as follows: 1: 80% ethanol, containing 0.50% vanillin and 1% Red 33; 2: 80% ethanol, containing 1% vanillin and 1% Red 33; and 3: 80% ethanol, containing 2% vanillin and 1% Red 33. A control solution containing 80% ethanol and 1% Red 33 was also included. The control and test solutions were exposed to light at an intensity of 765 Watts/m$^2$ for 6 hours. Referring to FIG. 7, the visual appearance of the test solutions changed markedly—top row, and the change in visual appearance appeared to be dependent on the concentration of the vanillin.

In a second series of experiments, the ability of stabilizers to prevent changes the stability of the dye Red 33 over time was investigated. Test solutions were as follows: 1: 80% ethanol, containing 0.50% vanillin, 0.1% Tinogard Q, and 1% Red 33; 2: 80% ethanol, containing 1% vanillin 0.1% Tinogard Q, and 1% Red 33; and 3: 80% ethanol, containing 2% vanillin, 0.1% Tinogard Q, and 1% Red 33. A control solution containing 80% ethanol 0.1% Tinogard Q, and 1% Red 33 was also included. The control and test solutions were exposed to light at an intensity of 765 Watts/m$^2$ for 6 hours. Referring to FIG. 7, the visual appearance of the test solutions changed—second row, and the change in visual appearance appeared to be dependent on the concentration of the vanillin.

In a third series of experiments, the ability of α-ketoglutaric acid to prevent changes the stability of the dye Red 33 over time was investigated. Test solutions were as follows: 1: 80% ethanol, containing 0.50% vanillin, 0.25% solution of an organic salt formed by reacting α-ketoglutaric acid with NMDA, and 1% Red 33; 2: 80% ethanol, containing 1% vanillin 0.25% solution of an organic salt formed by reacting α-ketoglutaric acid with NMDA, and 1% Red 33; and 3: 80% ethanol, containing 2% vanillin, 0.25% solution of an organic salt formed by reacting α-ketoglutaric acid with NMDA, and 1% Red 33 was also included. The control and test solutions were exposed to light at an intensity of 765 Watts/m² for 6 hours. Referring to FIG. 7, the visual appearance of the test solutions changed.

In a fourth series of experiments, the ability of stabilizers to prevent changes the stability of the dye Red 33 over time was investigated. Test solutions were as follows: 1: 80% ethanol, containing 0.50% vanillin, 0.3% Covabsorb, 0.1% Tinogard, and 1% Red 33; 2: 80% ethanol, containing 1% vanillin 0.3% Covabsorb, 0.1% Tinogard, and 1% Red 33; and 3: 80% ethanol, containing 2% vanillin 0.3% Covabsorb, 0.1% Tinogard, and 1% Red 33. A control solution containing 80% ethanol 0.3% Covabsorb, 0.1% Tinogard, and 1% Red 33 was also included. The control and test solutions were exposed to light at an intensity of 765 Watts/m² for 6 hours. Referring to FIG. 7, the visual appearance of the test solutions changed—fifth row, and the change in visual appearance appeared to be dependent on the concentration of the vanillin However, the presence of stabilizers appeared to reduce the change in visual appearance to some degree.

In a fifth series of experiments, the ability of α-ketoglutaric acid, in combination with stabilizers to prevent changes the stability of the dye Red 33 over time was investigated. Test solutions were as follows: 1: 80% ethanol, containing 0.50% vanillin, 0.3% Covabsorb, 0.1% Tinogard Q, 0.25% 0.25% solution of an organic salt formed by reacting α-ketoglutaric acid with NMDA, and 1% Red 33; 2: 80% ethanol, containing 1% vanillin, 0.3% Covabsorb, 0.1% Tinogard Q, 0.25% 0.25% solution of an organic salt formed by reacting α-ketoglutaric acid with NMDA, and 1% Red 33; and 3: 80% ethanol, containing 2% vanillin, 0.3% Covabsorb, 0.1% Tinogard Q, 0.25% 0.25% solution of an organic salt formed by reacting α-ketoglutaric acid with NMDA, and 1% Red 33. A control solution containing 80% ethanol 0.3% Covabsorb, 0.1% Tinogard Q, 0.25% 0.25% solution of an organic salt formed by reacting α-ketoglutaric acid with NMDA, and 1% Red 33 was also included. The control and test solutions were exposed to light at an intensity of 765 Watts/m² for 6 hours. Referring to FIG. 7, the visual appearance of the test solutions changed the least—sixth row.

The last row of FIG. 7 shows changes in the visual appearance of a control solution containing Red 33 and 0.25 to 1% solution of an organic salt formed by reacting α-ketoglutaric acid with NMDA. These data suggest that a concentration of 0.25% solution of an organic salt formed by reacting α-ketoglutaric acid with NMDA is sufficient to prevent alterations in the visual appearance of the dye.

Example 13

Prevention of the Light-Induced Oxidation of a Solution Containing a Perfume Raw Material According to Some Aspects Presented Herein In a first series of experiments, the effect of the concentration of the perfume raw material vanillin on the stability of the pH of the solution over time was investigated. Test solutions were as follows: 1: 80% ethanol, containing 0.50% vanillin and 1% Red 33; 2: 80% ethanol, containing 1% vanillin and 1% Red 33; and 3: 80% ethanol, containing 2% vanillin and 1% Red 33. A control solution containing 80% ethanol and 1% Red 33 was also included. The control and test solutions were exposed to light at an intensity of 765 Watts/m² for 6 hours. Referring to FIG. 11, the pH of the test solutions decreased markedly, with a change of 1.68 pH units—row labeled Control with Red 33.

In a second series of experiments, the ability of stabilizers to prevent changes the stability of the dye Red 33 over time was investigated. Test solutions were as follows: 1: 80% ethanol, containing 0.50% vanillin, 0.3% Covabsorb, and 1% Red 33; 2: 80% ethanol, containing 1% vanillin 0.3% Covabsorb, and 1% Red 33; and 3: 80% ethanol, containing 2% vanillin 0.3% Covabsorb, and 1% Red 33. A control solution containing 80% ethanol 0.3% Covabsorb, and 1% Red 33 was also included. The control and test solutions were exposed to light at an intensity of 765 Watts/m² for 6 hours. Referring to FIG. 11, the pH of the test solutions decreased markedly, with a change of 1.40 pH units—row labeled Red 33+0.3% Covabsorb.

In a third series of experiments, the ability of α-ketoglutaric acid, in combination with stabilizers to prevent changes the stability of the dye Red 33 over time was investigated. Test solutions were as follows: 1: 80% ethanol, containing 0.50% vanillin, 0.3% Covabsorb, 0.25% solution of an organic salt formed by reacting α-ketoglutaric acid with NMDA, and 1% Red 33; 2: 80% ethanol, containing 1% vanillin, 0.3% Covabsorb, 0.25% solution of an organic salt formed by reacting α-ketoglutaric acid with NMDA, and 1% Red 33; and 3: 80% ethanol, containing 2% vanillin, 0.3% Covabsorb, 0.25% solution of an organic salt formed by reacting α-ketoglutaric acid with NMDA, and 1% Red 33. A control solution containing 80% ethanol 00.3% Covabsorb, 0.25% solution of an organic salt formed by reacting α-ketoglutaric acid with NMDA, and 1% Red 33 was also included. The control and test solutions were exposed to light at an intensity of 765 Watts/m² for 6 hours. Referring to FIG. 11, the observed decrease in the pH of the test solutions was smaller, with a change of 0.02 pH units—row labeled Red 33+0.3% Covabsorb+0.25% α-ketoglutaric acid with NMDA, and 1% Red 33.

In a fourth series of experiments, the ability of stabilizers to prevent changes the stability of the dye Red 33 over time was investigated. Test solutions were as follows: 1: 80% ethanol, containing 0.50% vanillin, 0.3% Covabsorb, 0.1% Tinogard, and 1% Red 33; 2: 80% ethanol, containing 1% vanillin, 0.3% Covabsorb, 0.1% Tinogard, and 1% Red 33; and 3: 80% ethanol, containing 2% vanillin, 0.3% Covabsorb, 0.1% Tinogard, and 1% Red 33. A control solution containing 80% ethanol, 0.3% Covabsorb, 0.1% Tinogard, and 1% Red 33 was also included. The control and test solutions were exposed to light at an intensity of 765 Watts/m² for 6 hours. Referring to FIG. 11, the observed decrease in the pH of the test solutions was 0.66 pH units—row labeled Red 33+0.3% Covabsorb+0.1% Tinogard Q.

In a fifth series of experiments, the ability of α-ketoglutaric acid, in combination with stabilizers to prevent changes the stability of the dye Red 33 over time was investigated. Test solutions were as follows: 1: 80% ethanol, containing 0.50% vanillin, 0.3% Covabsorb, 0.1% Tinogard, 0.25% solution of an organic salt formed by reacting α-ketoglutaric acid with NMDA, and 1% Red 33; 2: 80% ethanol, containing 1% vanillin, 0.3% Covabsorb, 0.25% solution of an organic salt formed by reacting α-ketoglutaric acid with NMDA, and 1% Red 33; and 3: 80% ethanol, containing 2% vanillin 0.3% Covabsorb, 0.25% solution of an organic salt formed by reacting α-ketoglutaric acid with NMDA, and 1% Red 33. A control solution containing 80% ethanol 0.3% Covabsorb, 0.25% solution of an organic salt formed by reacting α-ketoglutaric acid with NMDA, and 1% Red 33was also included. The control and test solutions were exposed to light at an intensity of 765 Watts/m$^2$ for 6 hours. Referring to FIG. 11, the observed decrease in the pH of the test solutions was 0.07 pH units—row labeled Red 33+0.3% Covabsorb+0.1% Tinogard Q+0.25% solution of an organic salt formed by reacting α-ketoglutaric acid with NMDA.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A method of reducing light-induced oxidation of a formulated perfume, wherein the formulated perfume is a hydroalcoholic solution, or a perfumery raw material, wherein the formulated perfume or the perfumery raw material comprises a dye, the dye being selected from the group consisting of Red 4, Red 33, Yellow 5, Yellow 6, and Orange 4, and wherein the reduction of the light-induced oxidation reduces a discoloration of the formulated perfume or perfumery raw material, the method comprising:

adding at least one α-oxocarboxylic acid, wherein the at least one α-oxocarboxylic acid is α-ketoglutaric acid, and at least one stabilizer, wherein the at least one stabilizer is a mixture of butyl methoxydibenzoyl methane, ethylhexyl methoxycinnamate, ethylhexyl salicylate, and tris (tetramethylhydroxypiperidinol) citrate, to the formulated perfume or the perfumery raw material in an amount sufficient to reduce the light-induced oxidation of the formulated perfume or the perfumery raw material, wherein the reduction of the light-induced oxidation reduces a discoloration of the formulated perfume or perfumery raw material.

2. The method of claim 1, further comprising adjusting the pH of the formulated perfume or the perfumery raw material to a pH ranging from 5 to 7.5.

3. The method of claim 1, wherein the concentration of the at least one stabilizer in the formulated perfume or the perfumery raw material ranges from 0.01 wt % to 2 wt %.

4. The method of claim 1, wherein the amount sufficient of the at least one α-oxocarboxylic acid is a concentration ranging from 0.0001 weight percent to 10 weight percent, based on the total weight of the formulated perfume or the perfumery raw material.

5. The method of claim 1, wherein the at least one α-oxocarboxylic acid is added to the formulated perfume or perfumery raw material as a salt selected from the group consisting of: an organic salt, and a salt of a mono or divalent cation.

6. The method of claim 1, wherein the formulated perfume is a fine perfume, an Eau de Toilette, a cologne or an after-shave lotion.

\* \* \* \* \*